US008754865B2

(12) United States Patent
Merritt et al.

(10) Patent No.: US 8,754,865 B2
(45) Date of Patent: Jun. 17, 2014

(54) MEDICAL MEASURING SYSTEM AND METHOD

(71) Applicant: Volcano Corporation, San Diego, CA (US)

(72) Inventors: Fergus Merritt, El Dorado Hills, CA (US); Asher Cohen, Sacramento, CA (US); Duane De Jong, Elk Grove, CA (US); Gerald Lea Litzza, Sacramento, CA (US); Aaron Cheline, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/679,776

(22) Filed: Nov. 16, 2012

(65) Prior Publication Data
US 2013/0120297 A1    May 16, 2013

Related U.S. Application Data

(60) Provisional application No. 61/560,677, filed on Nov. 16, 2011.

(51) Int. Cl.
*G06F 3/041* (2006.01)
(52) U.S. Cl.
USPC ........... 345/173; 600/407; 600/437; 600/466; 600/467
(58) Field of Classification Search
CPC ....... G06F 1/1694; G06F 3/017; G06F 3/041; A61B 5/0066; A61B 8/12
USPC .................. 345/173; 600/407, 437, 466, 467
See application file for complete search history.

(56) References Cited

U.S. PATENT DOCUMENTS

| 5,590,219 A | * | 12/1996 | Gourdol | 382/202 |
| 5,812,188 A | * | 9/1998 | Adair | 348/77 |
| 6,273,857 B1 | | 8/2001 | Aden | |
| 6,597,808 B1 | * | 7/2003 | Guo et al. | 382/173 |
| 2002/0165005 A1 | * | 11/2002 | Travers et al. | 455/556 |

(Continued)

FOREIGN PATENT DOCUMENTS

WO    WO 2010-123858 A2    10/2010

OTHER PUBLICATIONS

"Mobile MIM liberates doctors to view CT & MRI scans on iPads and is FDA approved [App Review]" by F. Wodajo. iMedicalApps. http://www.imedicalapps.com/2011/04/mobile-mim-liberates-doctors-to-view-ct-mri-scans-wherever-they-are-and-is-fda-approved-app-review/. Apr. 13, 2011.*

(Continued)

*Primary Examiner* — Tse Chen
*Assistant Examiner* — Jason Ip
(74) *Attorney, Agent, or Firm* — Haynes and Boone, LLP

(57) ABSTRACT

A method of performing measurements on medical images with a bedside controller includes receiving, through a touch-sensitive display on the bedside controller, a user measurement input on an image displayed on the display, the user measurement input including a start point defined by a point of initial contact with the touch-sensitive display and an end point defined by a point of last contact with the touch-sensitive display. The method also includes selecting a measurement mode based on a shape of the user measurement input and calculating a measurement value associated with the user measurement input based on the measurement mode.

22 Claims, 13 Drawing Sheets

(56) References Cited

U.S. PATENT DOCUMENTS

| | | |
|---|---|---|
| 2006/0122514 A1 | 6/2006 | Byrd et al. |
| 2006/0274928 A1 | 12/2006 | Collins et al. |
| 2007/0146339 A1 | 6/2007 | Yang et al. |
| 2008/0004530 A1 | 1/2008 | Feldman et al. |
| 2008/0062122 A1* | 3/2008 | Rosenberg et al. ........... 345/156 |
| 2009/0051671 A1* | 2/2009 | Konstas ........................ 345/174 |
| 2009/0195514 A1* | 8/2009 | Glynn et al. .................. 345/173 |
| 2009/0299195 A1 | 12/2009 | Muller et al. |
| 2011/0009813 A1 | 1/2011 | Rankers |
| 2011/0128398 A1* | 6/2011 | Shimodaira ................ 348/222.1 |

OTHER PUBLICATIONS

International Searching Authority/Korean Intellectual Patent Office, "Notification of Transmittal of the International Search Report and The Written Opinion of the International Searching Authority, or the Declaration," for PCT/US2012/065293, mailed Feb. 20, 2013, 11 pages.

"True 3-Dimensional Reconstruction of Coronary Arteries in Patients by Fusion of Angiography and IVUS (ANGUS) and its Quantitative Validation" by C.J. Slager et al. Circulation. 102:511-516. 2000.

\* cited by examiner

MEDICAL MEASURING SYSTEM AND METHOD

CROSS-REFERENCE TO RELATED APPLICATIONS

This application claims the benefit of U.S. provisional patent application 61/560,677, filed Nov. 16, 2011, entitled "MEDICAL SENSING CONTROL SYSTEM AND METHOD," the entirety of which is incorporated by reference herein.

TECHNICAL FIELD

Embodiments of the present disclosure relate generally to the field of medical devices and, more particularly, to a medical measuring system and associated methods of use.

BACKGROUND

Innovations in diagnosing and verifying the level of success of treatment of disease have progressed from solely external imaging processes to include internal diagnostic processes. In addition to traditional external image techniques such as X-ray, MRI, CT scans, fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy. Traditionally, many of these procedures are carried out by a multitude of physicians and clinicians, where each performs an assigned task. For example, a physician may stand next to a patient in the sterile field and guide the insertion and pull back of an imaging catheter. A clinician near the physician may control the procedure workflow with a controller, for example by starting and stopping the capture of images. Further, after images have been captured, a second clinician in an adjacent control room working at a desktop computer may select the images of interest and make measurements on them. Typically, the physician in the catheter lab must instruct the clinician in the control room on how to make such measurements. This may lengthen the time of the procedure, increase the cost of the procedure, and may lead to measurement errors due to miscommunication or clinician inexperience. Further, when making measurements on medical sensing images, a clinician may typically have to select a measurement mode prior to making any measurements, reducing the efficiency of the medical sensing workflow.

Accordingly, while the existing devices and methods for conducting medical sensing workflows have been generally adequate for their intended purposes, they have not been entirely satisfactory in all respects.

SUMMARY

In one exemplary aspect, the present disclosure is directed to a method of performing measurements on medical images with a bedside controller. The method includes receiving, through a touch-sensitive display on the bedside controller, a user measurement input on an image displayed on the display, the user measurement input including a start point defined by a point of initial contact with the touch-sensitive display and an end point defined by a point of last contact with the touch-sensitive display. The method also includes selecting a measurement mode based on a shape of the user measurement input and calculating a measurement value associated with the user measurement input based on the measurement mode.

In some instances, the method of performing measurements may include selecting one of a diameter measurement mode and an area measurement mode based on the shape of the user measurement input.

In another exemplary aspect, the present disclosure is directed to a bedside controller. The bedside controller includes a housing, the housing including self-contained mounting structure, a touch-sensitive display disposed within a surface of the housing and configured to display images and receive user input on the surface, a processor disposed within the housing, and a communication module disposed within the housing, communicatively coupled to the processor, and configured to transmit and receive medical data from a processing system. The bedside controller also includes a non-transitory computer readable storage module disposed within the housing, communicatively coupled to the processor, and including a plurality of instructions stored therein and executable by the processor. The plurality of instructions include instructions for receiving, through the touch-sensitive display, a user measurement input on an image displayed on the display, instructions for selecting a measurement mode based on a shape of the user measurement input, and instructions for calculating a measurement value associated with the user measurement input based on the measurement mode.

In another exemplary aspect, the present disclosure is directed to a medical measuring system. The medical procedure workflow system includes a medical sensor device configured to gather medical data from a patient and a processing system communicatively coupled to the medical sensor device and operable to receive the medical data from the medical sensor device, the processing system being further operable to transform the medical data into medical images representative of the patient. The system also includes a bedside controller communicatively coupled to the processing system and operable to receive the medical images from the processing system and display the medical images on a touch-sensitive display, the bedside controller being further configured to receive, through the touch-sensitive display, a user measurement input on a medical image displayed on the display, select a measurement mode based on a shape of the user measurement input, and calculate a measurement value associated with the user measurement input based on the measurement mode.

In some instances, the bedside controller may be configured to receive the user measurement input while in a sterile field surrounding the patient. Additionally, the bedside controller may be configured to select one of a diameter measurement mode and an area measurement mode based on the shape of the user measurement input.

DETAILED DESCRIPTION

Figure 1:
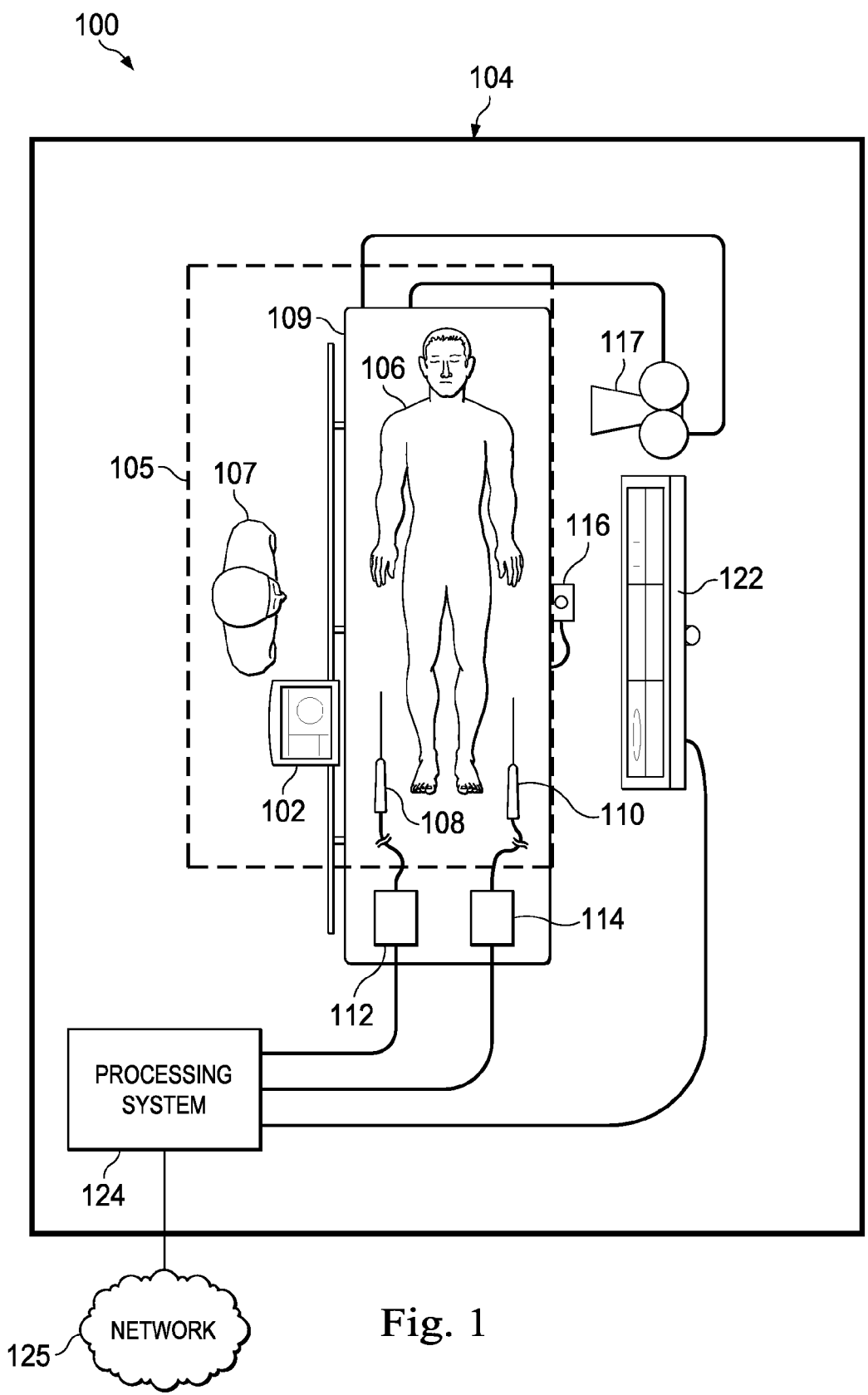
FIG. 1 is a schematic drawing depicting a medical sensing system including a bedside controller according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

FIG. 1 is a schematic drawing depicting a medical sensing system 100 including a bedside controller 102 according to one embodiment of the present disclosure. In general, the medical sensing system 100 provides for coherent integration and consolidation of multiple forms of acquisition and processing elements designed to be sensitive to a variety of methods used to acquire and interpret human biological physiology and morphological information. More specifically, in system 100, the bedside controller 102 is a touch-enabled, integrated computing device for the acquisition, control, interpretation, measurement, and display of multi-modality medical sensing data. In the illustrated embodiment, the bedside controller 102 is a tablet-style touch-sensitive computer that provides user controls and diagnostic images on a single surface. In the medical sensing system 100, the bedside controller 102 is operable to present workflow control options and patient image data via graphical user interfaces (GUIs) corresponding to a plurality of medical sensing modalities. The bedside controller 102 will be described in greater detail in association with FIGS. 3A, 3B, and 4.

In the illustrated embodiment, the medical sensing system 100 is deployed in a catheter lab 104. The catheter lab 104 may be used to perform on a patient 106 any number of medical sensing procedures alone or in combination such as, by way of example and not limitation, angiography, intravascular ultrasound (IVUS), virtual histology (VH), forward looking IVUS (FL-IVUS), intravascular photoacoustic (IVPA) imaging, fractional flow reserve (FFR) determination, coronary flow reserve (CFR) determination, optical coherence tomography (OCT), computed tomography, intra-cardiac echocardiography (ICE), forward-looking ICE (FLICE), intravascular palpography, transesophageal ultrasound, or any other medical sensing modalities known in the art. In addition to controlling medical sensing systems, the bedside controller may be used to cooperate with and control medical treatment systems such as, for example but without limitation, those used for stent placement, coil embolism, ablation therapy, kidney stone treatments, basket placement in a cystoscopy, tumor removal, and chemical therapies. The catheter lab 104 further includes a sterile field 105 that encompasses the portions of the catheter lab surrounding the patient 106 on a procedure table 109 and a clinician 107, who may perform any number of medical sensing procedures or treatments. As shown in FIG. 1, the bedside controller 102 may be positioned within the sterile field 105 and may be utilized by the clinician 107 to control a workflow of a medical sensing procedure or treatment being performed on the patient 106. For example, the clinician 107 may initiate the procedure workflow, watch real-time IVUS images captured during the procedure, and make measurements on the IVUS images all using the bedside controller 102 inside of the sterile field 105. In alternative embodiments, the bedside controller 102 may be utilized outside of the sterile field 105, for instance, in other locations within the catheter lab 104 or in a control room adjacent to the catheter lab. A method of utilizing the bedside controller 102 to control a medical sensing workflow or treatment workflow will be discussed in greater detail in association with FIGS. 7 and 8.

In the embodiment illustrated in FIG. 1, the medical sensing system 100 additionally includes a number of interconnected medical sensing-related tools in the catheter lab 104 to facilitate a multi-modality workflow procedure, such as an IVUS catheter 108, an IVUS patient isolation module (PIM) 112, an OCT catheter 110, and OCT PIM 114, an electrocardiogram (ECG) device 116, an angiogram system 117, a boom display 122, and a multi-modality processing system 124. The bedside controller 102, PIMs 112 and 114, ECG device 116, angiography system 117, and boom display 122 are communicatively coupled to the processing system 124. In one embodiment, the processing system 124 is a computer workstation with the hardware and software to acquire, process, and display multi-modality medical sensing data, but in other embodiments, the processing system may be any other type of computing system operable to process medical sensing data. For example, during an IVUS workflow, the processing system 124 is operable to accept raw IVUS data from the IVUS PIM 112, transform it into IVUS images, and make the images available to the bedside controller 124, so that they may be displayed to the clinician 107 for analysis. In the embodiments in which the processing system 124 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller. Further, the multi-modality processing system 124 is communicatively coupled to a data network 125. In the illustrated embodiment, the data network 125 is a TCP/IP-based local area network (LAN), however in other embodiments, it may utilize a different protocol such as Synchronous Optical Networking (SONET), or may be a wide area network (WAN). The processing system 124 may connect to various resources via the network 125, such as a Digital Imaging and Communications in Medicine (DICOM) system, a Picture Archiving and Communication System (PACS), and a Hospital Information System. U.S. Patent Application No. 61/473,570, entitled "MULTI-MODALITY MEDICAL SENSING SYSTEM AND METHOD" and filed on Apr. 8, 2011, discloses a multi-modality processing system that processes medical sensing data and is hereby incorporated by reference in its entirety.

In the medical sensing system 100, the IVUS PIM 112 and OCT PIM 114 are operable to respectively receive medical sensing data collected from the patient 106 by the IVUS catheter 108 and OCT catheter 110 and are operable to transmit the received data to the processing system 124. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. Additionally, the ECG device 116 is operable to transmit electrocardiogram signals or other hemodynamic data from patient 106 to the processing system 124. To aid the clinician in data capture, the bedside controller 102 is operable to display the ECG data along side medical sensing data. Further, in some embodiments, the processing system 124 may be operable to synchronize data collection with the catheters 108 and 110 using ECG signals from the ECG 116. Further, the angiogram system 117 is operable to collect x-ray, computed tomography (CT), or magnetic resonance images (MRI) of the patient 106 and transmit them to the processing system 124. After the x-ray, CT, or MRI data has been processed into human-readable images by the processing system 124, the clinician 107 may navigate the GUI on the bedside controller 124 to retrieve the images from the processing system 124 and display them on the controller. In some embodiments, the processing system 124 may co-register image data from angiogram system 117 (e.g. x-ray data, MRI data, CT data, etc.) with sensing data from the IVUS and OCT catheters 108 and 110. As one aspect of this, the co-registration may be performed to generate three-dimensional images with the sensing data. Such co-registered 3-D images data may be viewable on the bedside controller 124. In one embodiment, a clinician may rotate, zoom, and otherwise manipulate such 3-D images on the bedside controller 102 using simultaneous touch inputs (i.e. multitouch) and gestures.

Additionally, in the illustrated embodiment of FIG. 1, medical sensing tools in system 100, are communicatively coupled to the processing system 124 via a wired connection such as a standard copper link or a fiber optic link. Specifically, the bedside controller 124 may be communicatively and/or electrically coupled to the processing system 124 via a Universal Serial Bus (USB) connection, a Power-over-Ethernet connection, a Thunderbolt connection, a FireWire connection, or some other high-speed data bus connection.

Figure 2:
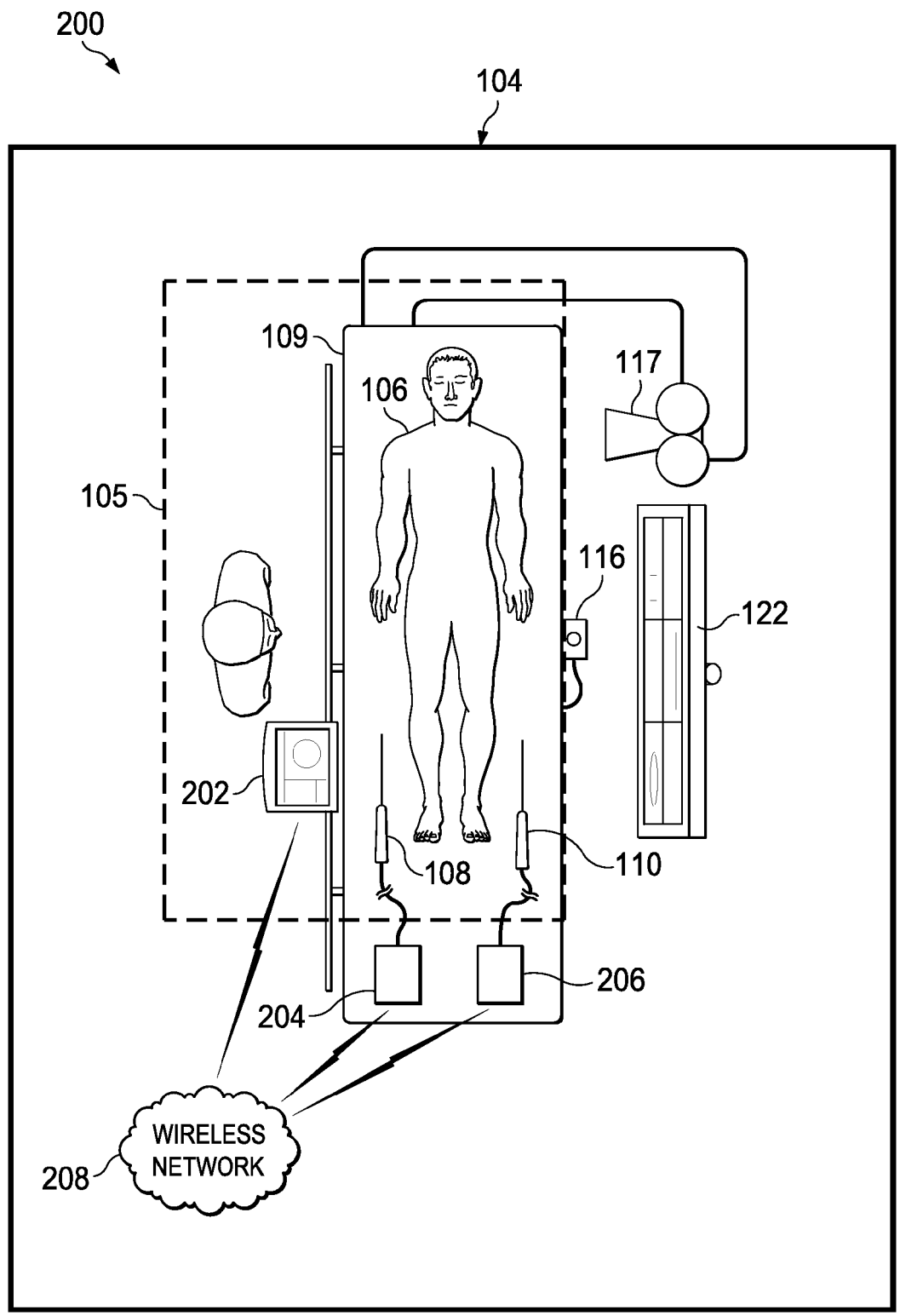
FIG. 2 is a schematic drawing depicting a medical sensing system including a wireless bedside controller according to another embodiment of the present disclosure.

However, in an alternative embodiment, such as that shown in FIG. 2, the medical sensing tools may communicate wirelessly. In that regard, FIG. 2 is a schematic drawing depicting a medical sensing system 200 including a wireless bedside controller 202 according to another embodiment of the present disclosure. The medical sensing system 200 is similar to the system 100 of FIG. 1 but the medical sensing tools including the wireless bedside controller 202, a wireless IVUS PIM 204, and a wireless OCT PIM 206 communicate with a wireless network 208 via wireless networking protocols. For example, the bedside controller 202 may send and receive workflow control parameters, medical sensing images, and measurement data to and from a remote processing system via IEEE 802.11 Wi-Fi standards, Ultra Wide-Band (UWB) standards, wireless FireWire, wireless USB, Bluetooth, or another high-speed wireless networking standard. Such wireless capability allows the clinician 107 to more freely position the bedside controller 202 inside or outside of the sterile field 105 for better workflow management.

Figure 3A:
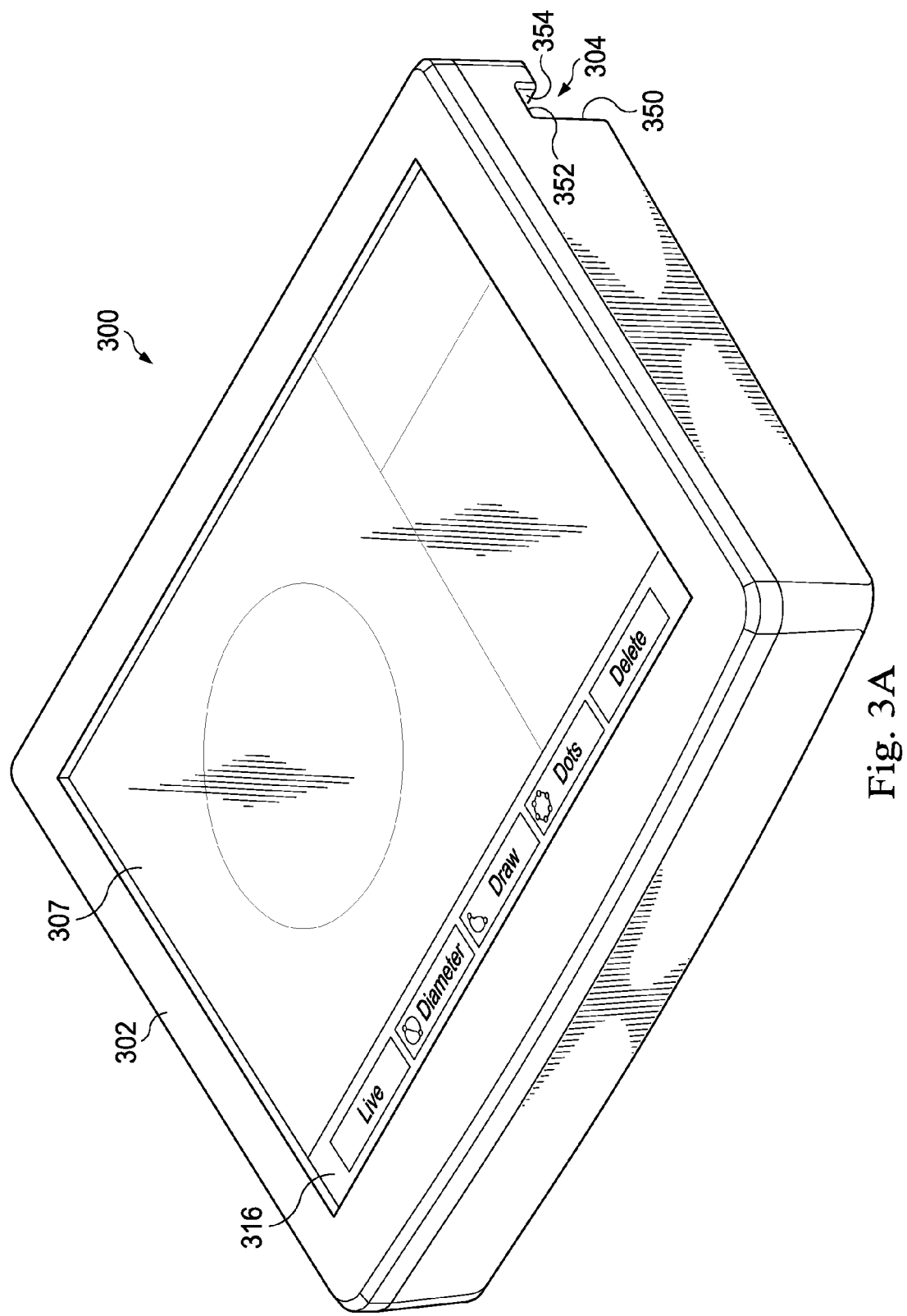
FIG. 3A is a diagrammatic perspective view of a bedside controller.
Figure 3B:
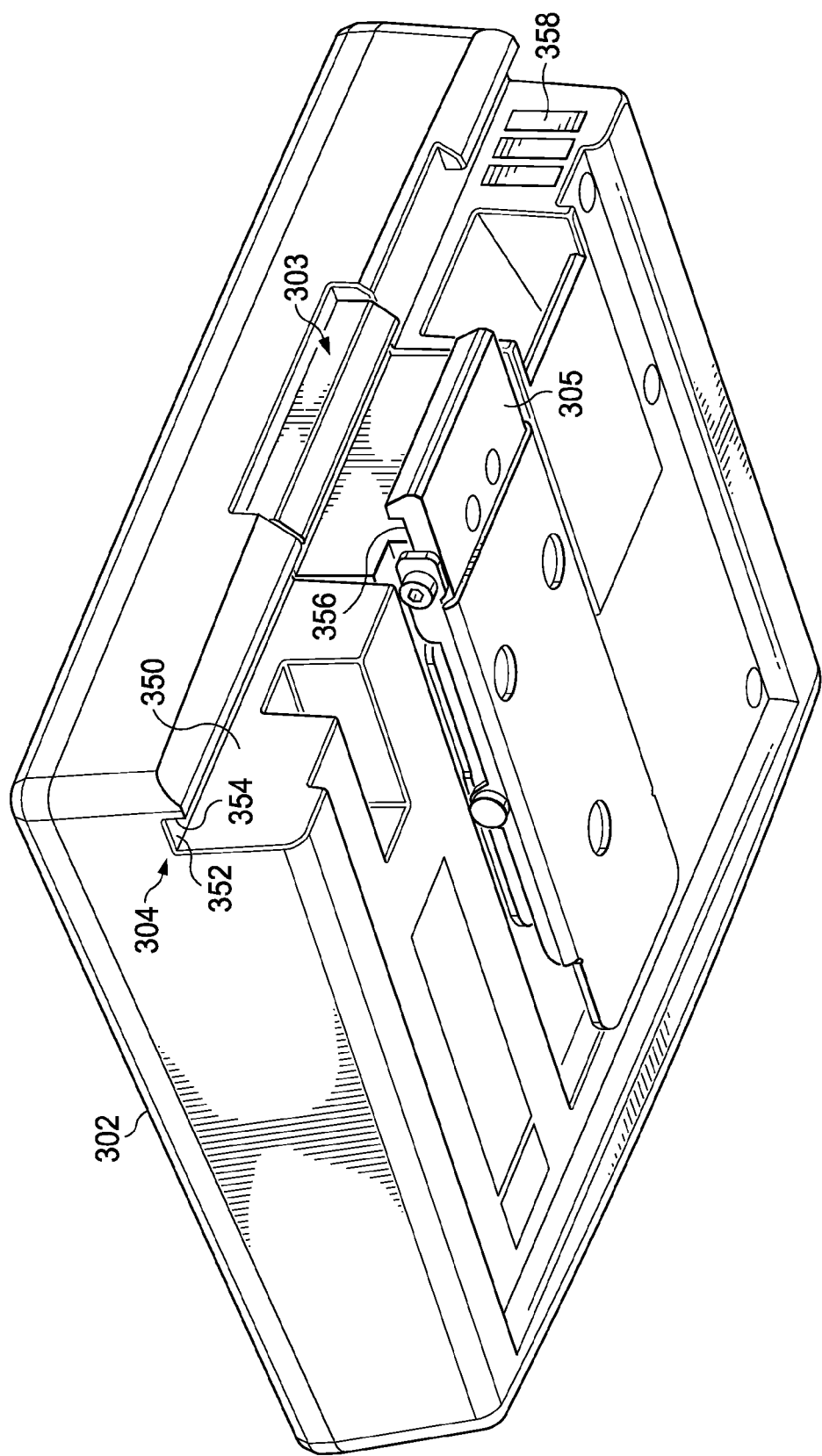
FIG. 3B is a diagrammatic rear perspective view of the bedside controller of FIG. 3A.
Figure 3C:
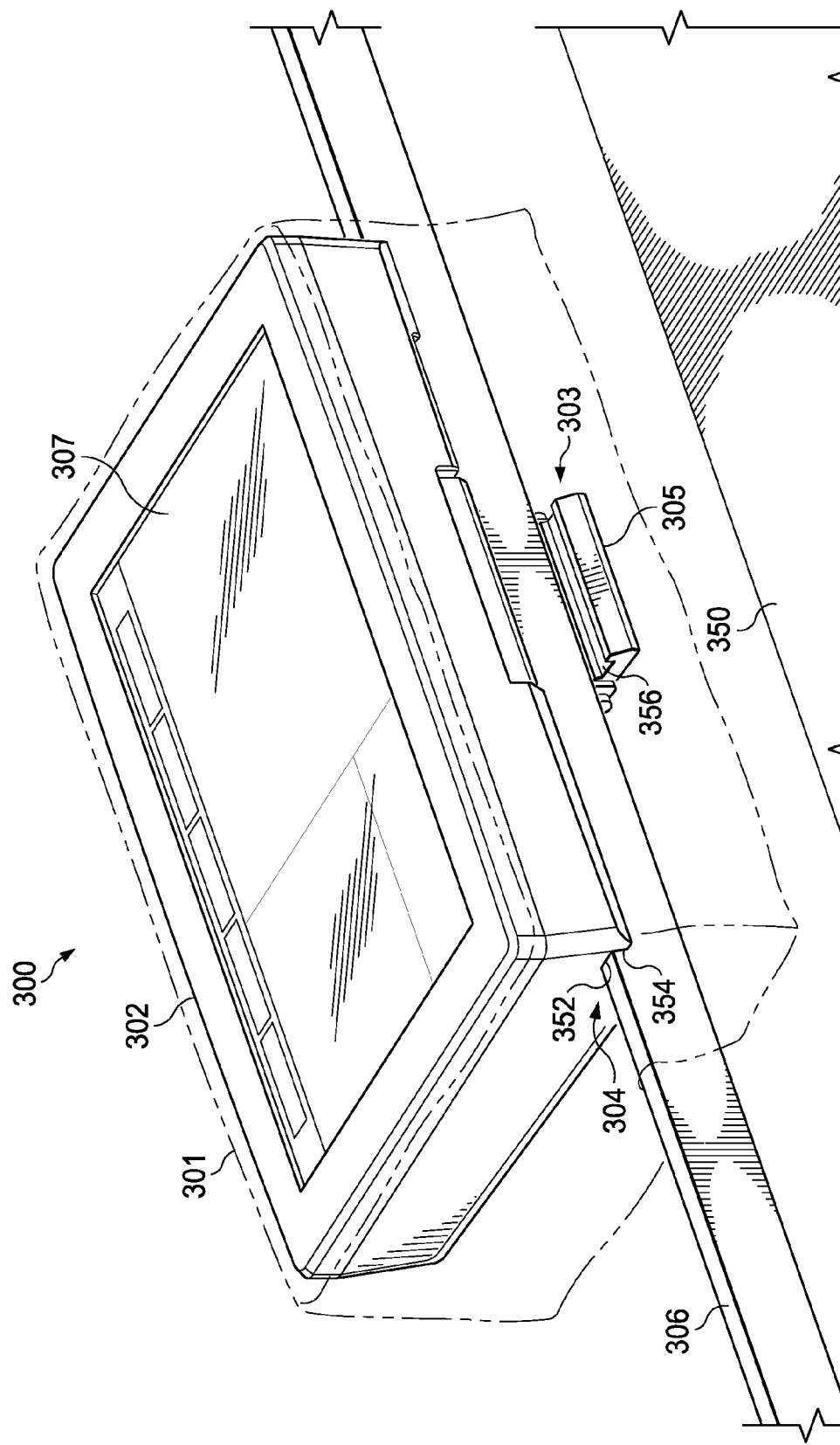
FIG. 3C is a diagrammatic perspective view of the bedside controller of FIG. 3A mounted to a bed rail.
Figure 4:
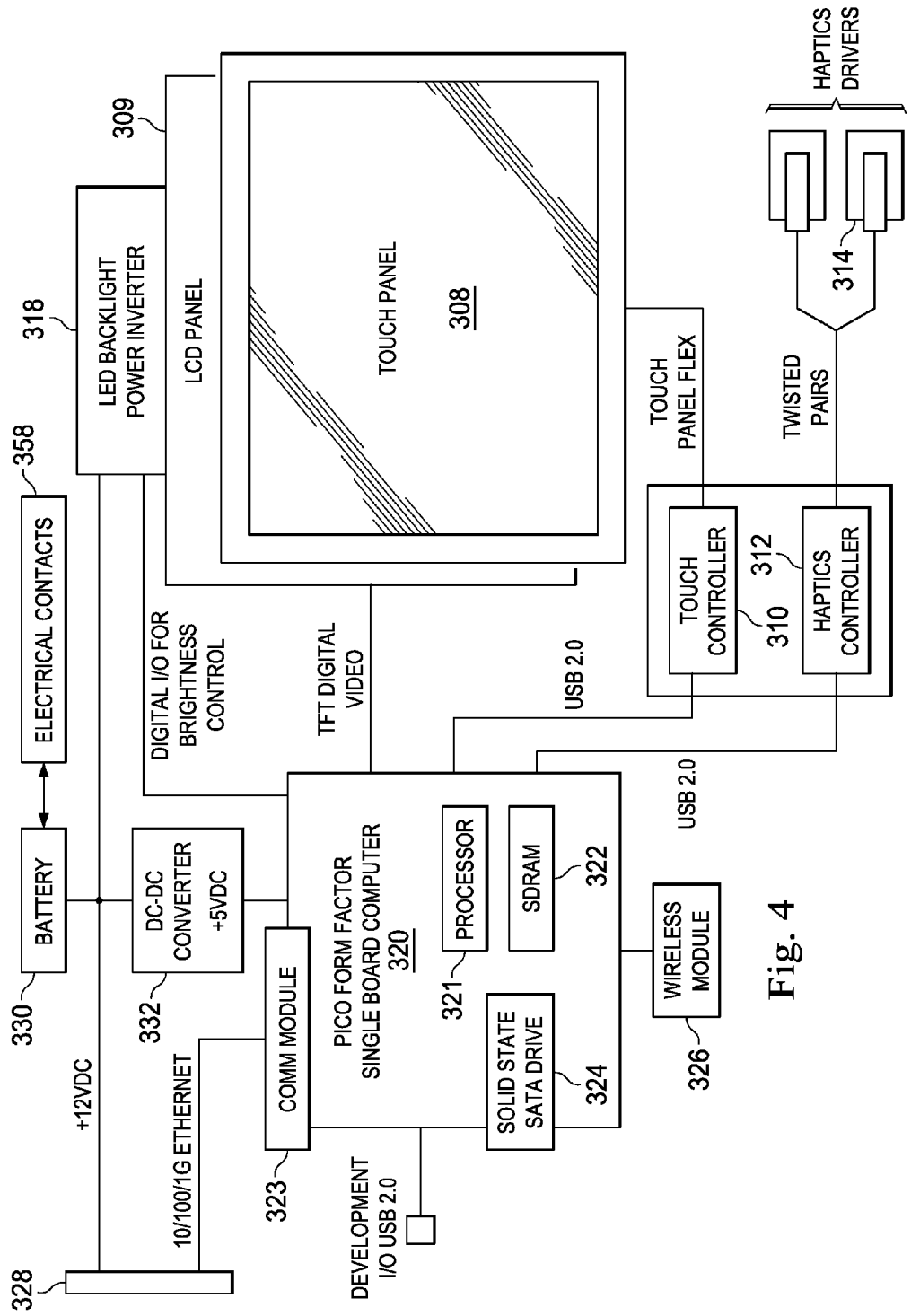
FIG. 4 is a functional block diagram of the bedside controller of FIGS. 3A and 3B according to aspects of the present disclosure.

With reference now to FIGS. 3A, 3B, 3C and 4, FIG. 3A is a diagrammatic perspective view of a bedside controller 300, FIG. 3B is a diagrammatic rear perspective view of the bedside controller, FIG. 3C is a diagrammatic perspective view of the bedside controller mounted to a bed rail, and FIG. 4 is a functional block diagram of the bedside controller 300 according to aspects of the present disclosure. The bedside controller 300 is similar to the bedside controllers 102 and 202 in medical sensing systems 100 and 200, and is operable to, among other things, initiate a medical sensing or treatment procedure workflow, display real-time images captured during the procedure, and accept measurement input on the images from a clinician. The bedside controller 300 generally improves system control available to a clinician working at a patient table. For instance, giving a clinician both workflow control and measurement capability within the sterile field reduces errors and improves workflow efficiency.

As show in FIG. 3A, the bedside controller 300 includes an integrally formed housing 302 that is easy to grasp and move around a catheter lab or other medical setting. In one embodiment, the integrally formed housing 302 may be seamlessly molded from materials such as thermoplastic or thermosetting plastic or moldable metal. In other embodiments, the integrally formed housing 302 may comprise a plurality of housing portions fixedly bonded in a substantially permanent manner to form an integral housing. The housing 302 is resistant to fluids, and, in one embodiment, may have a rating of IPX4 against fluid ingress as defined by the International Electrotechnical Commission (IEC) standard 60529. In other embodiments in which the housing 302 may be used in different environments, the hub may have a different fluid ingress rating. In the illustrated embodiment, the housing 302 is about 10.5 inches in width, about 8.25 inches in height, and has as thickness of about 2.75 inches. In alternative embodiments, the housing may have a different width, height, or thickness that is similarly conducive to portability.

As shown in FIG. 3B, the housing 302 further includes self-contained mounting structure 303 disposed on the housing. In the illustrated embodiment, the mounting structure is disposed near an outer edge of the housing. The mounting structure 303 allows the bedside controller 300 to be releasably mounted in a variety of places in and out of a catheter lab in a self-contained manner. That is, the bedside controller 300 may be directly secured to another object without the use of a separate external mount. In the illustrated embodiment, the mounting structure 303 includes a mounting channel 304 and a retaining clamp 305 that pivots over the mounting channel to secure a mounting platform therewithin. The mounting channel 304 is defined by a longer front wall 350, a top wall 352, and a shorter back wall 354, and the retaining clamp includes a slot 356 that extends through the clamp in a manner generally parallel to the mounting channel. The front wall 350 and the back wall 354 are generally perpendicular to a touch-sensitive display 307 in the housing 302, and the top wall 352 is generally parallel to the display 307. In the illustrated embodiment, the retaining clamp is spring-loaded and releasably exerts pressure on objects situated in the mounting channel. In alternative embodiments, the retaining clamp may be configured differently and exert force via mechanisms other than springs.

As shown in FIG. 3C, in operation, the bedside controller 300 may be releasably secured to a mounting platform, for example a bed rail 306, by pivoting the mounting clamp 305 to an open position, positioning the controller such that the rail extends through the length of the channel 304, and releasing the clamp such that it secures the rail within the channel. When the rail 306 is positioned in the mounting channel 304 and the clamp 305 is holding it therein, three surfaces of the rail are respectively engaged by the front wall 350, the top wall 352, and the back wall 354, and a fourth surface of the rail extends through the slot 356 in the clamp 305. In this manner, the mounting structure 303 may maintain the bedside controller 300 in a position generally parallel to a procedure table 350 associated with the bed rail 306, as shown in FIG. 3B. Described differently, the mounting structure 303 is a cantilevered mounting structure in that it secures one end of the controller to an object while the majority of the controller extends away from the object in an unsupported manner. Such a cantilevered position allows for a display of the controller to be both readable and at a comfortable input angle for an operator. Further, the self-contained mounting structure 303 allows the bedside controller 300 to be quickly released from the bed rail 306 and reattached to an IV pole, a cart on which a processing system is deployed, or other location in or out of the sterile field to allow for convenient workflow control and image analysis. In alternative embodiments the mounting structure 303 of the bedside controller may vary from the design illustrated in FIGS. 3A and 3B and include additional and/or different components to allow for self-contained mounting.

Embedded into the front of the housing 302 is the touch-sensitive display 307 that comprises both a touch panel 308 and a flat panel display 309. The touch panel 308 overlays the flat panel display 308 and accepts user input via human touch, stylus touch, or some other analogous input method. In other words, the touch-sensitive display 307 displays images and accepts user input on the same surface. In the current embodiment, the touch panel 308 is a resistive-type panel, but in alternative embodiments it may be a capacitive-type panel, projective-type panel, or some other suitable type of touch enabled input panel. Further, the touch panel 308 is operable to accept multiple inputs simultaneously (multitouch), for instance, to enable rotation of a three-dimensional rendering of a vessel along multiple axes. Additionally, the touch panel 308 is capable of receiving input when a sterile drape 301 is covering the bedside controller 300 and also when a user is gloved. The touch panel 308 is controlled by a touch controller 310 disposed within the housing 302. Further, when a clinician makes contact with the touch panel 308, the touch panel is operable to provide haptic feedback via a haptics controller 312 and haptics drivers 314. This haptic technology is operable to simulate a plurality of sensations on the touch panel 308 by varying the intensity and frequency of vibrations generated when a user contacts the touch panel. In some embodiments, the housing 302 may include a sheath configured to store a stylus therein. Thus, a clinician may remove the stylus from the sheath in the housing to make measurements on the bedside controller and store it when the measurements have been completed.

Beneath the touch panel 308 is the flat panel display 309 that presents a graphical user interface (GUI) 316 to a user. In the illustrated embodiment, the flat panel display 309 is a LCD display but in alternative embodiments, it may be a different type of display such an LED display or an AMOLED display. In the illustrated embodiment, the flat panel display 309 is illuminated by a LED backlight power inverter 318. As mentioned above, the GUI 316 not only allows a clinician to control a medical sensing workflow but also make measurements on images captured from a patient in the sterile field. A method of interacting with the GUI 316 to make vessel measurements will be discussed in greater detail in association with FIGS. 8-11.

The bedside controller 300 includes a single board processing platform 320 within the housing 302 that is operable to render the GUI 316 and process user input. In the illustrated embodiment, the processing platform has a pico form factor and includes integrated processing components such as a processor 321, system memory 322, graphics processing unit (GPU), communications module 323, and I/O bus controller. In some embodiments, the processor 321 may be a low power processor such as an Intel Atom® processor or a ARM-based processor, and the communications module 323 may be a 10/100/1 Gb Ethernet module. And, the I/O bus controller may be a Universal Serial Bus (USB) controller. The bedside controller 300 further includes a storage module 324 that is a non-transitory computer readable storage medium operable to store an operating system (i.e. software to render and control the GUI), image manipulation software, medical sensing data and images received from a processing system, and other medical sensing-related software. The processor 321 is configured to execute software and instructions stored on the storage module 324. In the illustrated embodiment, the storage module 324 is a solid state drive (SSD) hard drive communicatively coupled to the processing platform 320 via a SATA connection, but, in alternative embodiments, it may be any other type of non-volatile or temporary storage module. The bedside controller 300 further includes a wireless communications module 326 communicatively coupled to the processing platform 320. In some embodiments, the wireless communications module is a IEEE 802.11 Wi-Fi module, but in other may be a Ultra Wide-Band (UWB) wireless module, a wireless FireWire module, a wireless USB module, a Bluetooth module, or another high-speed wireless networking module.

In the illustrated embodiment, the bedside controller 300 is powered via both a wired 12 VDC power-over-Ethernet (PoE) connection 328 and a battery 330 disposed within the housing 302. In one embodiment, the battery 330 may be sealed within the integrally formed housing 302 and may be recharged through electrical contacts disposed on the exterior of the housing and electrically coupled to the battery. As shown in the embodiment of FIG. 3B, the front wall 350 may include one or more electrical contacts 358 through which the battery 330 may be charged when the controller is mounted to objects with compatible charging structure. In other embodiments, the housing 302 may include a battery compartment with a removable cover to permit battery replacement. Such a battery compartment cover may be resistant to fluid ingress (e.g., with an IPX4 rating). The beside controller 300 may be coupled to a processing system in the catheter lab via the PoE connection 328, over which it receives medical sensing images that have been captured from the patient and rendered on the processing system. In operation, when the bedside controller is coupled to the PoE connection 328, it receives power and communications over the same physical wire. When the bedside controller 300 is disconnected from the PoE connection 328, it runs on battery power and receives data wirelessly via the wireless communications module 326. When used wirelessly in a catheter lab, the beside controller may directly communicate with a processing system (i.e. in an ad-hoc wireless mode), or, alternatively, it may communicate with a wireless network that serves a plurality of wireless devices. In alternative embodiments, the bedside controller 300 may receive power and data through different wired connections, or receive data communications through a wired data connection and power from the battery 330, or receive data communications through the wireless module 326 and power from a wired electrical connection. In some embodiments, the bedside controller 300 may be used in a semi-wireless configuration, in which the battery 330 provides backup power to the controller when the controller is temporarily disconnected from a wired power source. For example, if at the beginning of a procedure, the bedside controller 300 is connected to a PoE connection (or other type of wired connection) and during the procedure the controller must be disconnected from the PoE connection to allow for a cabling adjustment, the battery 330 may keep the controller alive until a PoE connection can be re-established. In this manner, a full power-off and reboot of the controller 300 is avoided during a procedure. As shown in FIG. 4, a DC-DC power converter 332 converts input voltage to a voltage usable by the processing platform 320.

It is understood that although the bedside controller 300 in the illustrated embodiments of FIGS. 3 and 4 includes specific components described herein, the bedside controller may include any number of additional components, for example a charge regulator interposed between the electrical contacts and the battery, and may be configured in any number of alternative arrangements in alternative embodiments.

Figure 5:
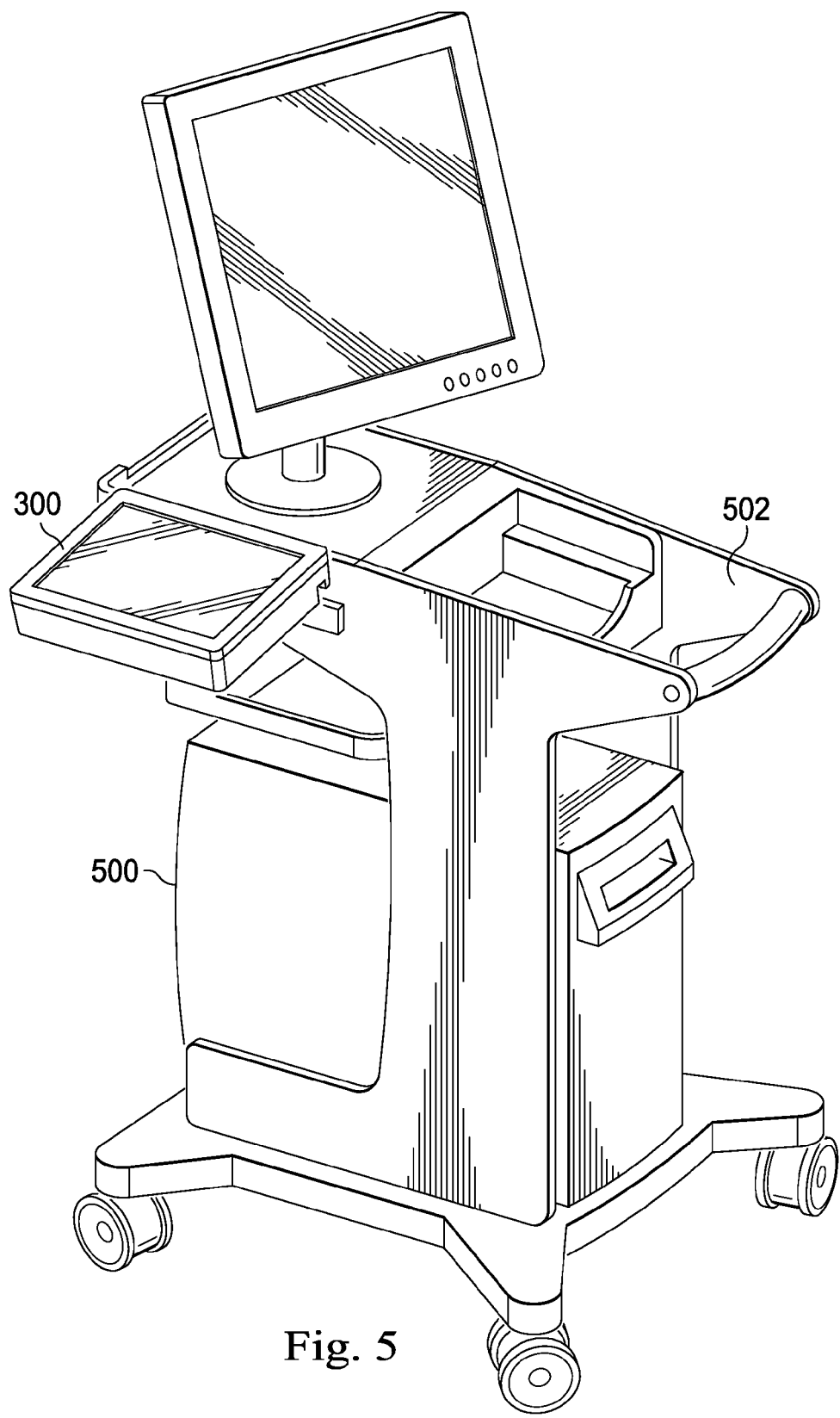
FIG. 5 is a diagrammatic perspective view of a multi-modality mobile processing system with the bedside controller of FIGS. 3A and 3B attached thereto.
Figure 6:
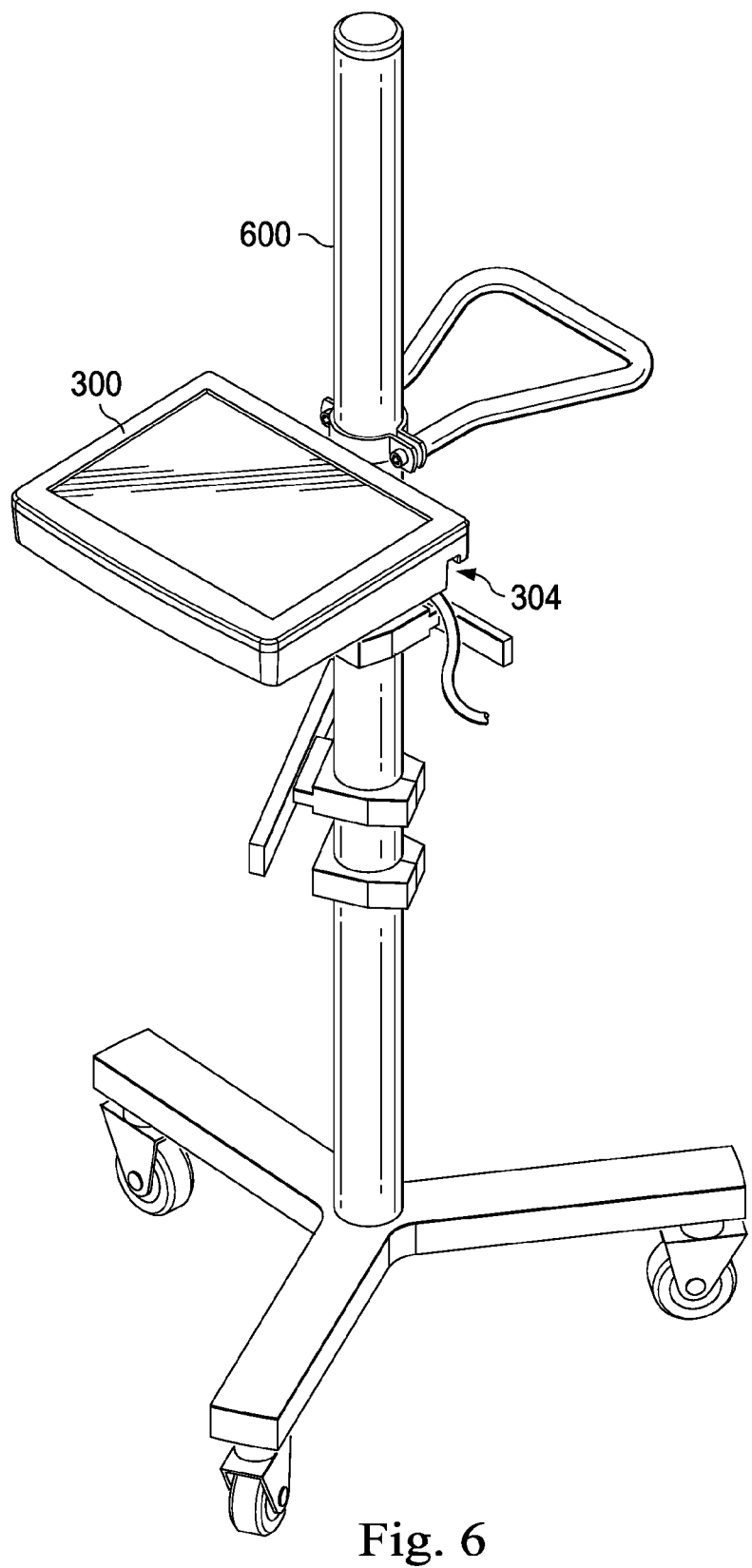
FIG. 6 is a diagrammatic perspective view of the bedside controller of FIGS. 3A and 3B releasably mounted on an IV pole.

With reference now to FIGS. 5 and 6, illustrated are examples of locations in which the bedside controller 300 may be mounted. FIG. 5 is a diagrammatic perspective view of a multi-modality mobile processing system 500. The processing system 500 is disposed on a cart 502 that enables the processing system to be easily moved between different locations such as different catheter labs. As shown in FIG. 5, the bedside controller 300 is mounted to the cart 502 so that it may be transported to catheter labs with the processing system. The bedside controller 300 is releasably secured to the cart via the self-contained mounting structure 303 that is built into the housing 302. Further, in some embodiments, the cart 502 may include a dock for the bedside controller 300 such that when the controller is docked on the cart its battery is recharged through the electrical contacts 358 disposed on the housing 302. As shown in FIG. 6, the bedside controller 300 may also releasably attach to an IV pole 600 via the self-contained mounting structure 303. When so attached, the bedside controller 300 may be rolled next to a patient in the sterile field and thus within reach of a clinician who may operate the controller with a single hand.

Figure 7:
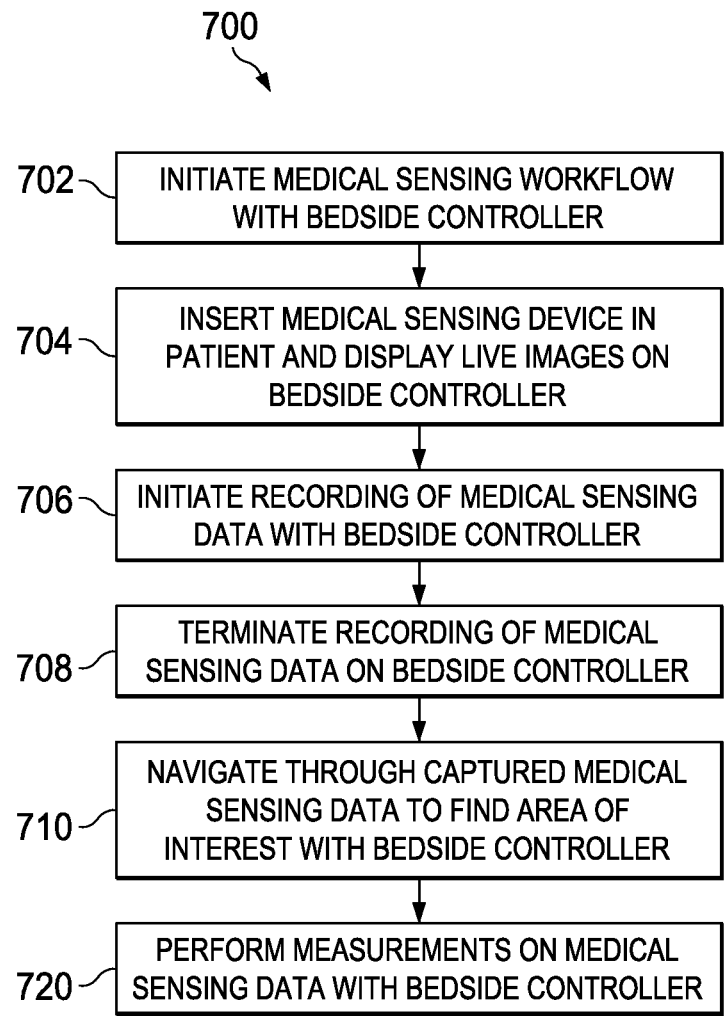
FIG. 7 is a high-level flowchart illustrating a method of conducting a medical sensing workflow with a bedside controller according to various aspects of the present disclosure.

FIG. 7 is a high-level flowchart illustrating a method 700 of conducting a medical sensing workflow with the bedside controller 300 of FIGS. 3-4 according to various aspects of the present disclosure. The method 700 will be described in the context of an IVUS procedure but may equally apply to any number of medical sensing or treatment procedures, such as an OCT procedure, a FLIVUS procedure, an ICE procedure, etc. The method 700 begins at block 702 where a medical sensing workflow is initiated with the bedside controller 300. Using an IVUS procedure as an example, a clinician in the sterile field and adjacent a patient may select the "IVUS" option out of a plurality of modes (e.g., OCT, Chromaflow, FLIVUS, etc) on the bedside controller's GUI to begin the IVUS workflow. Next, in block 704, after an IVUS imaging catheter has been inserted into the patient, the clinician may select a 'Live Images' option on the bedside controller's GUI to receive live images from the catheter. Using the real-time images, the clinician may guide the catheter within the patient to a desired position. In typical embodiments, a processing system may collect raw IVUS data from the catheter and process the data to render IVUS images. The bedside controller retrieves the IVUS images from the processing system and displays them to a user in real-time. Then, in block 706, after the IVUS catheter has been appropriately positioned in the patient using the live images, the clinician selects a 'Record' option on the bedside controller GUI and begins the catheter pull back. The processing system responds to the record command and begins rendering and storing IVUS images. The method 700 proceeds to block 708 where, after the IVUS catheter pull back has been completed, the clinician terminates the recording of IVUS images via the bedside controller's GUI. Then, in block 710, the clinician at the bedside recalls the captured IVUS images on the bedside controller and finds the IVUS images associated with the area of interest. Specifically, the bedside controller may present a condensed view of all captured images and the clinician may navigate through them using gestures on the bedside controller's touch panel to find the target area. Finally, in block 720, the clinician performs measurements on the IVUS images directly on the bedside controller. The user of the bedside controller creates measurements by interacting with an image through a series of presses, moves and releases using a finger or stylus on the controller's touch-sensitive display. These actions are interpreted by the bedside controller's internal processor and converted to measurements on the display. For precise measurements, the clinician may annotate the images using a stylus or another tool compatible with the bedside controller's touch panel. After the appropriate measurements have been completed, the clinician may save the images to the processing system by selecting the appropriate options in the bedside controller GUI. A method of performing measurements on the bedside controller will be described below.

Figure 8:
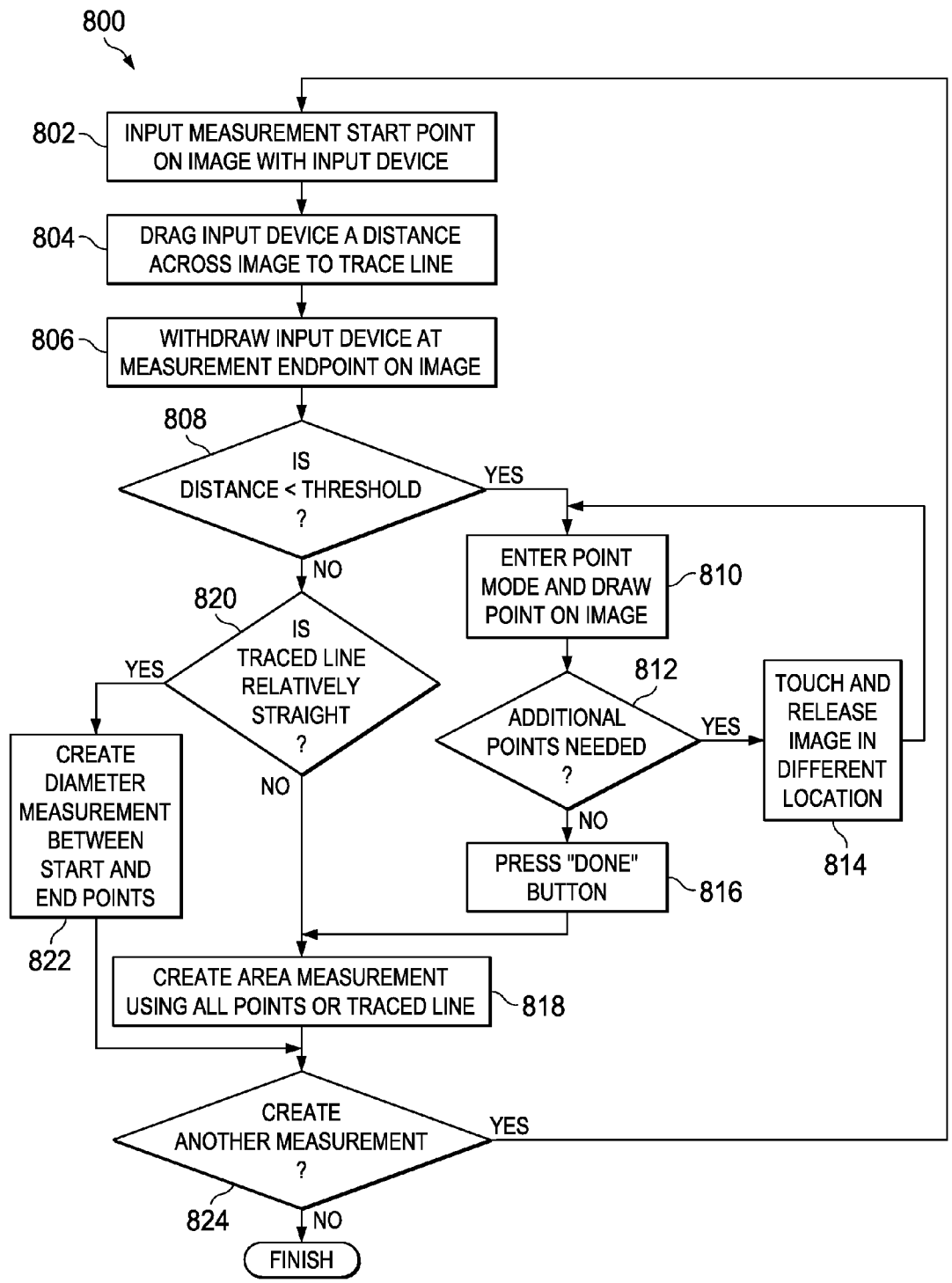
FIG. 8 is high-level flowchart of a method that describes a measurement workflow conducted on a bedside controller according to various aspects of the present disclosure.

FIG. 8 is high-level flowchart of a method 800 that describes a measurement workflow on the bedside controller 300 of FIGS. 3A-4. In one embodiment, the method 800 may be carried out during block 720 of the method 700 in FIG. 7 as part of a medical sensing workflow on intravascular images. Further, in the illustrated embodiment, the method 800 of making measurements on the bedside controller 300 is implemented in measurement software stored in the storage module 324 in the bedside controller. In general, when measuring images, such as intravascular images, a clinician has the option of making different types of measurements such as diameter measurements and area measurements. Typically, when making area measurements, a clinician may either denote the edges of an object by drawings a series of discrete points that are connected in subsequent processing or by drawing a continuous line around the object to the measured. In this regard, the method 800 of performing measurements on images is "smart" in that it does not require a user to select a particular measurement mode prior to interacting with an image on the bedside controller. For instance, when a user performs a series of measurement inputs on the bedside controller, the GUI software interprets the nature (e.g. shape) of a user's measurement inputs, automatically enters either diameter mode, area-point mode or area-draw mode, and outputs the desired measurement on the controller's display.

In more detail, the method 800 begins at block 802 where an image to be measured is displayed on the bedside controller and a user inputs a measurement start point on the image with an input device. For example, the user may use a finger or stylus to indicate a point on a vessel border from which a measurement will commence. Note that prior to selecting the measurement start point, the measurement software did not require the user to select a measurement mode. Next, in block

Figure 9:
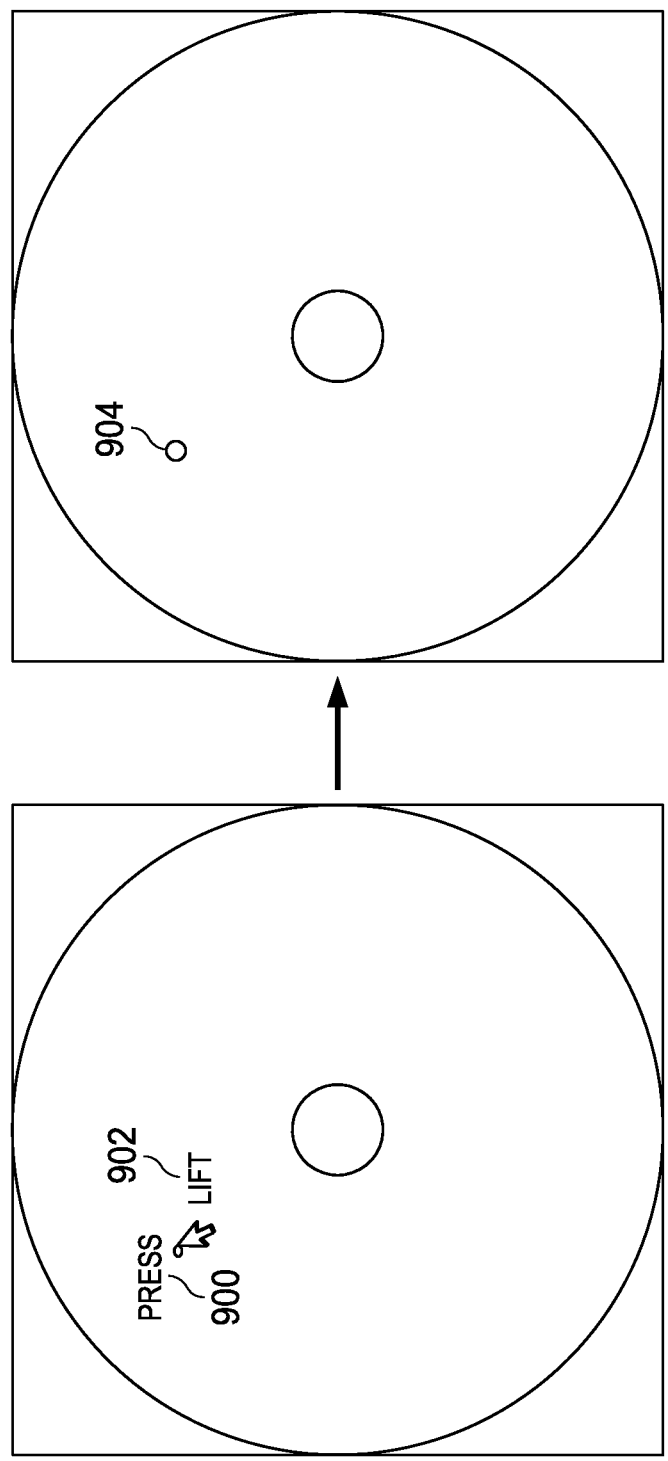
FIGS. 9-11 are partial screen images illustrating various aspects of the method of FIG. 8.

804, the user, without removing the input device from the image after indicating the start point, drags the input device across the image a distance to trace a line. Then, in block 806, the user withdraws the input device from the image at a measurement end point. The method 800 proceeds to decision block 808 where the measurement software determines whether the distance between the start point and the end point is less than a threshold value. In one embodiment, the threshold value is equivalent to 10 pixels, but, in alternative embodiments, the threshold value may be smaller or larger or measured in different units. Further, in some embodiments, the threshold value is adjustable either manually by a user or automatically based on detected error rates. If the distance is less than the threshold value, the method proceeds to block 810 where the measurement software enters area-point mode and draws a point on the image corresponding to the end point (i.e. where the user lifted the input device from the touch-enabled display). This sequence is illustrated in FIG. 9. Specifically, when a user presses (900) an input device on an image and immediately lifts (902) the input device, the input will be interpreted as a point entry and a point 904 will be drawn on the image.

The method 800 then proceeds to decision block 812 where it is decided whether additional points are needed to make a measurement on the image. If additional points are needed, the method proceeds to block 814 where a user touches and releases the displayed image at a different location. Note that in this branch of method 800, the measurement software is in area-point mode so that all entries will be interpreted as points and, when an input is detected, a point will be drawn on the image in block 810 regardless of the distance between a start point and end point of the input. If no additional points are needed to make a measurement in decision block 812, the method 800 proceeds to block 816, where a user selects a 'Done' button in the bedside controller GUI to exit area-point mode. In block 818, the measurement software creates an area measurement using the entered points. For example, in an embodiment directed toward vessel measurement, the measurement software connects the entered points to create a bounding circle at the vessel's outer edge. In one embodiment, the measurement software uses the entered points as seed points to assist edge detection algorithms.

Figure 10:
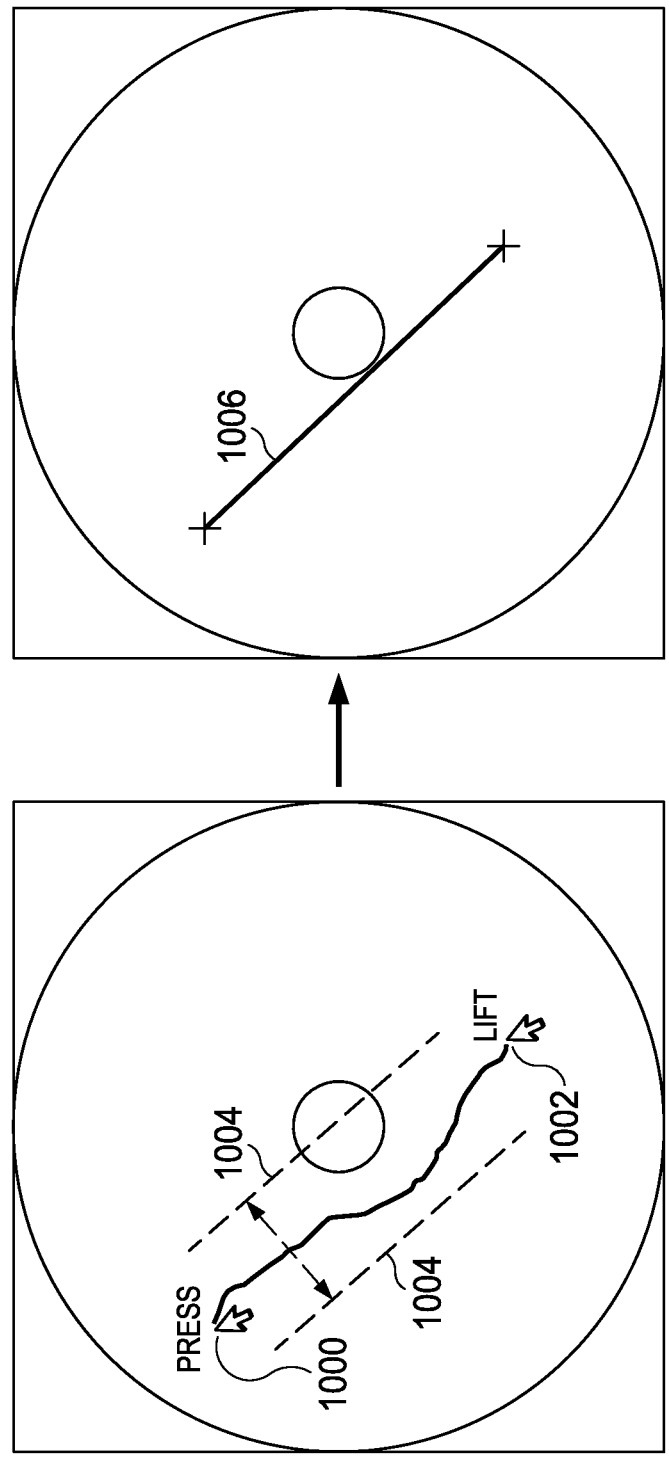
Figure 11:
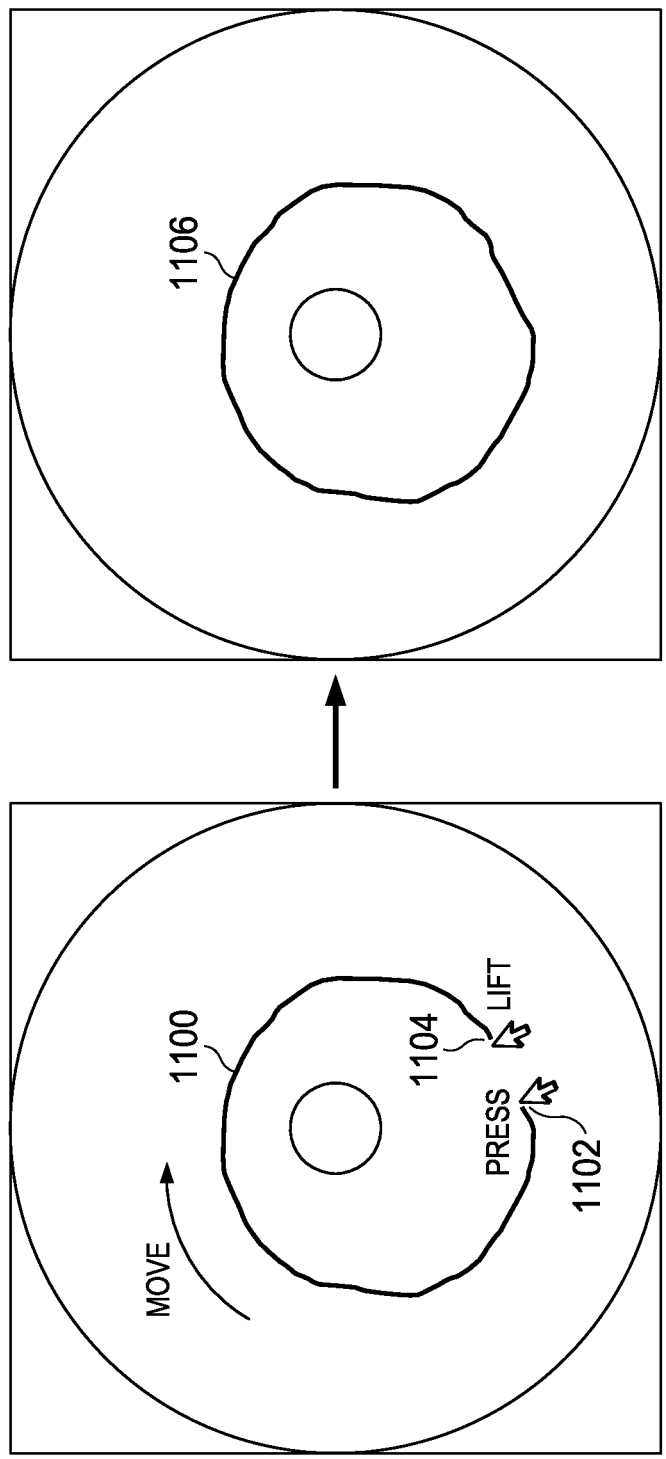

With reference back to decision block 808, if the distance between the start point and the end point is greater than or equal to the threshold, the method 800 proceeds to decision block 820 where the measurement software determines whether the drawn line is "relatively straight". That is, it determines whether the user desires to measure a diameter with a line or an area with a enclosed shape. As shown in FIG. 10, to make such a determination, the measurement software compares intervening points on the traced line between a start point 1000 and an end point 1002 against a boundary threshold 1004. If all intervening points are within the boundary threshold 1004, the measurement software determines that the user desires to make a diameter measurement and transforms the traced line into a straight line 1006 extending from the start point to the end point. The diameter measurement is thus based on the length of the straight line 1006. In alternative embodiments, however, the measurement software may employ different methods for determining whether the user desires to make a diameter measurement or an area measurement, such as detecting whether intervening points between start and end points increase in distance from the start point before decreasing in distance from the start point or detecting whether the traced line extending through the start point, at least one intervening point, and the end point is arcuate past a threshold degree. At decision block 820, if the user's traced line is relatively straight, the method proceeds to block 822 where the measurement software enters diameter mode and outputs a measurement of the straight line 1006 created between the start and end points. If, however, the traced line is not relatively straight, the method 800 proceeds to 818 where the measurement software enters area-draw mode. As shown in FIG. 11, the traced line 1100 between start point 1102 and end point 1104 extends outside of a boundary threshold (not shown) and is thus not relatively straight, prompting the measurement software to enter area-draw mode. Once this determination is made, the software connects the start and ends points to create a unbroken bounding line 1006 from which an area may be calculated. After an area measurement has been made in block 818 (either in area-point mode or area-draw mode), the method proceeds to decision block 824 where it is determined if another measurement needs to be done. If so, the method proceeds back to block 802 where a user selects another start point on the image without first selecting a measurement mode. If all measurements have been completed, the method 800 ends.

It is understood that the methods 700 and 800 illustrated in the flow charts of FIGS. 7 and 8 may, in alternative embodiments, be performed in a different order and may include different and/or additional blocks in some embodiments. For example, workflows for some medical sensing procedure may allow for additional measurement modes, such as volumetric measurements. According to the described aspects of the present disclosure, a user may initiate any such additional measurement modes without first selecting a measurement mode, thus simplifying the workflow. Further, the steps in methods 700 and 800 described above may be completed over the course of more than one patient visit to a catheter lab.

Although illustrative embodiments have been shown and described, a wide range of modification, change, and substitution is contemplated in the foregoing disclosure and in some instances, some features of the present disclosure may be employed without a corresponding use of the other features. For example, in some embodiments, the touch-enabled integrated bedside controllers 102 and 300 may be used to control and measure non-cardiovascular diagnostic data such as data from cranial or peripheral arteries, as well as data from non-vascular body portions. Further, the controllers 102 and 300 may be used to control an MRI workflow and measure MRI image data, or may be utilized in computer assisted surgery (CAS) applications. Further, the modules described above in association with the bedside controller 300 may be implemented in hardware, software, or a combination of both. And the bedside controller may be designed to enable user control in many different network settings such as ad-hoc networks, local area networks, client-server networks, wide area networks, internets, and the controller may have a number of form factors such as a tablet, a smartphone, a laptop, or any other similar device. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of performing measurements on medical images with a bedside controller, the method comprising:
   receiving, through a touch-sensitive display on the bedside controller, a user measurement input on an intravascular image displayed on the display, the intravascular image obtained in real time by an intravascular imaging device within a vessel of a patient, the intravascular imaging device including at least one of an ultrasound transducer and an optical coherence tomography (OCT) component, wherein the intravascular imaging device is controlled by the bedside controller, and wherein the user measurement input includes a start point on the intravascular image defined by a point of initial contact with the touch-sensitive display and an end point on the intravascular image defined by a point of last contact with the touch-sensitive display;

selecting a measurement mode from a group of measurement modes including a diameter measurement mode, an area-point measurement mode, and an area-draw measurement mode based on the user measurement input without requiring a user to select the measurement mode prior to making the user measurement input on the touch-sensitive display, wherein selecting the measurement mode includes:

determining if a distance between the start point and the end point is less than a threshold distance;

selecting an area-point measurement if the distance between the start point and the end point is less than the threshold distance;

determining, when the distance between the start point and the end point is greater than a threshold distance, if any intervening points along the user measurement input between the start point and the end point fall outside of a boundary threshold;

selecting the diameter measurement mode if none of the intervening points fall outside of the boundary threshold; and selecting the area-draw measurement mode if at least one intervening point falls outside of the boundary threshold;

calculating a measurement value associated with the user measurement input based on the selected measurement mode; and displaying the calculated measurement value on the touch-sensitive display.

2. The method of claim 1, wherein selecting the measurement mode includes selecting one of the diameter measurement mode, the area-point measurement mode, and the area-draw measurement mode based on the shape of the user measurement input.

3. The method of claim 1,
wherein, in response to selecting the diameter measurement mode, a straight line is drawn between the start point and the end point; and
wherein calculating the measurement value includes calculating the length of the straight line.

4. The method of claim 1,
wherein selecting the area-point or area-draw measurement mode includes connecting the start point and the end point to create a bounded object; and
wherein calculating the measurement value includes calculating the area of the bounded object.

5. The method of claim 1, wherein, after selecting the area-point measurement mode, the method further includes determining whether additional points are needed to calculate an area measurement value on the intravascular image.

6. The method of claim 5, wherein, after selecting the area-point measurement mode, the method further includes:
interpreting subsequent user measurement inputs as points; and
connecting the points to create a bounded object;
wherein calculating the measurement value includes calculating the area of the bounded object.

7. The method of claim 1, wherein receiving the user measurement input includes detecting contact on the touch-sensitive display from one of a stylus and a body part.

8. The method of claim 1, wherein receiving the user measurement input includes detecting contact on the touch-sensitive display through one of a sterile drape and a glove.

9. A bedside controller, comprising:
a housing, the housing including self-contained mounting structure;
a touch-sensitive display disposed within the housing and configured to display real-time intravascular images obtained by an intravascular imaging device disposed within a vessel of the patient and receive user input on the touch-sensitive display, wherein the intravascular imaging device includes at least one of an ultrasound transducer and an optical coherence tomography (OCT) component;
a processor disposed within the housing;
a communication module disposed within the housing, communicatively coupled to the processor and the intravascular imaging device disposed within the vessel, and configured to transmit and receive medical data from a processing system, the medical data including the real-time intravascular images obtained by the intravascular imaging device; and
a non-transitory computer readable storage module disposed within the housing, communicatively coupled to the processor, and including a plurality of instructions stored therein and executable by the processor, the plurality of instructions including:
instructions for receiving, through the touch-sensitive display, a user measurement input on an intravascular image displayed on the display, the user measurement input including a start point on the intravascular image defined by a point of initial contact with the touch-sensitive display and an end point on the intravascular image defined by a point of last contact with the touch-sensitive display;
instructions for selecting a measurement mode based on the user measurement input without requiring a user to select the measurement mode prior to making the user measurement input on the touch-sensitive display, wherein the measurement mode is selected from a group of measurement modes including a diameter measurement mode, an area-point measurement mode, and an area-draw measurement mode by:
determining if a distance between the start point and the end point is less than a threshold distance;
selecting an area-point measurement if the distance between the start point and the end point is less than the threshold distance;
determining, when the distance between the start point and the end point is greater than a threshold distance, if any intervening points along the user measurement input between the start point and the end point fall outside of a boundary threshold;
selecting the diameter measurement mode if none of the intervening points fall outside of the boundary threshold; and
selecting the area-draw measurement mode if at least one intervening point falls outside of the boundary threshold;
instructions for calculating a measurement value associated with the user measurement input based on the selected measurement mode; and
instructions for displaying the calculated measurement value on the touch-sensitive display.

10. The bedside controller of claim 9, wherein the touch-sensitive display is configured to accept user input through a sterile drape.

11. The bedside controller of claim 9, wherein the touch-sensitive display is configured to accept user input from gloved touch.

12. The bedside controller of claim 9, wherein the touch-sensitive display is configured to provide haptic feedback to a user.

13. The bedside controller of claim 9, wherein the housing is fluid resistant.

14. The bedside controller of claim 9, wherein the communication module is a wireless communication module.

15. The bedside controller of claim 9, including a rechargeable battery disposed within the housing, the battery being configured to provide power to the non-transitory computer readable storage module, the communication module, the processor, and the touch-sensitive display.

16. The bedside controller of claim 15, wherein the bedside controller is configured to dock to a processing system and draw power therefrom to recharge the battery.

17. The bedside controller of claim 9, wherein the instructions for selecting the measurement mode include instructions for selecting one of a diameter measurement mode, the area-point measurement mode, and an area-draw measurement mode based on the shape of the user measurement input.

18. The bedside controller of claim 9,
wherein the instructions for selecting the measurement mode include instructions for drawing a straight line between the start point and the end point when the diameter measurement mode is selected; and
wherein the instructions for calculating the measurement value include instructions for calculating the length of the straight line when the diameter measurement mode is selected.

19. The bedside controller of claim 9,
wherein the instructions for selecting the measurement mode include instructions for connecting the start point and the end point to create a bounded object when the area-point or area-draw measurement mode is selected; and
wherein the instructions for calculating the measurement value include instructions for calculating the area of the bounded object when the area-point or area-draw measurement mode is selected.

20. A medical measuring system, comprising:
a medical sensor device configured to gather intravascular medical data from a patient;
a processing system communicatively coupled to the medical sensor device and operable to receive the intravascular medical data from the medical sensor device, wherein the medical sensor device includes at least one of an ultrasound transducer and an optical coherence tomography (OCT) component, the processing system being further operable to transform the intravascular medical data into real-time intravascular medical images representative of the patient; and
a bedside controller communicatively coupled to the processing system and operable to receive the real-time intravascular medical images from the processing system and display the real-time intravascular medical images on a touch-sensitive display, the bedside controller being further configured to:
receive, through the touch-sensitive display, a user measurement input on a intravascular medical image displayed on the display, the user measurement input including a start point on the intravascular medical image defined by a point of initial contact with the touch-sensitive display and an end point on the intravascular medical image defined by a point of last contact with the touch-sensitive display;
select a measurement mode from a group of measurement modes including a diameter measurement mode, an area-point measurement mode, and an area-draw measurement mode based on the user measurement input without requiring a user to select the measurement mode prior to making the user measurement input on the touch-sensitive display, wherein selecting the measurement mode includes:
determining if a distance between the start point and the end point is less than a threshold distance;
selecting an area-point measurement if the distance between the start point and the end point is less than the threshold distance;
determining, when the distance between the start point and the end point is greater than a threshold distance, if any intervening points along the user measurement input between the start point and the end point fall outside of a boundary threshold;
selecting the diameter measurement mode if none of the intervening points fall outside of the boundary threshold; and
selecting the area-draw measurement mode if at least one intervening point falls outside of the boundary threshold; and
calculate a measurement value associated with the user measurement input based on the selected measurement mode.

21. The medical measuring system of claim 20, wherein the bedside controller is configured to select one of the diameter measurement mode, the area-point measurement mode, and the area-draw measurement mode based on the shape of the user measurement input.

22. The medical measuring system of claim 20, wherein the bedside controller is configured to control the commencement and termination of a recordation of medical data captured by the medical sensor device.

* * * * *